| United States Patent [19] | [11] | 4,237,223 |
|---|---|---|
| Metz | [45] | Dec. 2, 1980 |

[54] SHEET FOR PICKING OFF MICROORGANISMS

[75] Inventor: Harald Metz, Bickenbach, Fed. Rep. of Germany

[73] Assignee: Merck Patent Gesellschaft mit beschränkter Haftung, Darmstadt, Fed. Rep. of Germany

[21] Appl. No.: 31,802

[22] Filed: Apr. 20, 1979

[30] Foreign Application Priority Data

Apr. 21, 1978 [DE] Fed. Rep. of Germany ....... 2817503

[51] Int. Cl.³ .............................................. C12Q 1/24
[52] U.S. Cl. ..................................... 435/30; 428/315; 428/343; 435/292; 435/293; 435/805
[58] Field of Search .................... 435/30, 29, 34, 292, 435/293, 294, 287, 296, 299, 803, 805, 31, 32, 39; 73/150 R; 15/104 A; 428/315, 343

[56] References Cited

U.S. PATENT DOCUMENTS

| 1,901,094 | 3/1933 | Gabosch | 428/343 X |
|---|---|---|---|
| 2,904,474 | 9/1959 | Förg | 435/30 X |
| 2,985,554 | 5/1961 | Dickard | 428/343 X |
| 3,085,572 | 4/1963 | Blackford | 428/343 X |
| 3,661,718 | 5/1972 | Sterling | 435/30 X |
| 3,751,341 | 8/1973 | Seitz et al. | 435/30 X |
| 3,819,467 | 6/1974 | Kovac | 428/343 X |
| 3,846,248 | 11/1974 | Rose | 435/30 X |

*Primary Examiner*—Robert J. Warden
*Attorney, Agent, or Firm*—Millen & White

[57] ABSTRACT

A method of determining the presence of microorganisms on a surface comprises contacting the surface to be tested for the presence of microorganisms with an adhesive side of a sheet consisting essentially of a porous, flexible support material having an adhesive surface on at least one side such that when contacted with a microorganism-containing surface, the microorganisms will be adhered thereto; removing the sheet from this surface; placing the sheet on a sterile culture medium for microorganisms, the side placed on the medium being that opposite the side which was in contact with the test surface; incubating the sheet; and analyzing the incubated sheet for the presence of microorganisms.

A sheet for use in the method comprises a porous, flexible support material having an adhesive surface on at least one side and which is sterile throughout, said adhesive surface being such that when contacted with a microorganism-containing surface, the microorganisms will be adhered thereto.

12 Claims, No Drawings

SHEET FOR PICKING OFF MICROORGANISMS

BACKGROUND OF THE INVENTION

The present invention relates to a sheet for picking off microorganisms from a surface and to a procedure for identifying or determining the presence of microorganisms using this sheet.

Pick-off culture media are used for the identification of microorganisms on surfaces, for example, on walls and on and in equipment, furniture, apparatus, fittings, installations, etc. These culture media usually consist of a layer of an aqueous culture medium jelly, usually based on agar-agar, on a suitable support. German Auslegeschrift 1,013,837 discloses, for example, absorbent supports, such as paper, textile fabric or plastics having a porous structure, as culture medium supports which are used for picking off microorganisms. To use these devices, the support provided with the culture medium, which is kept moist, is pressed against the surface to be tested. It is then removed and incubated at a suitable temperature until the microorganisms have become visible as colonies.

The known pick-off culture media have, however, a number of disadvantages. Moist culture media have only a limited stability and require special storage conditions. The pick-off operation on surfaces which are sensitive to moisture or on surfaces which withdraw water from the moist culture medium is problematical. Moreover, there is a high probability that microorganisms will not be taken up, or at least will not be take up in a sufficient amount, upon simply being brought into contact with a moist medium.

SUMMARY OF THE INVENTION

Accordingly, it is an object of this invention to provide a sheet for picking off microorganisms from surfaces, the sheet being dry and thus of unlimited stability; with which removal of the microorganisms can be effected even from surfaces which are sensitive to moisture; and which is suitable for all applications.

In a method aspect, the present invention relates to a method of determining the presence of microorganisms on a surface which comprises contacting the surface to be tested for the presence of microorganisms with an adhesive side of a sheet consisting essentially of a porous, flexible support material having an adhesive surface on at least one side such that when contacted with a microorganism-containing surface, the microorganisms will be adhered thereto; removing the sheet from this surface; placing the sheet on a sterile culture medium for microorganisms, the side placed on the medium being that opposite the side which was in contact with the test surface; incubating the sheet; and analyzing the incubated sheet for the presence of microorganisms.

In a composition aspect, the present invention relates to a sheet for use in the method which comprises a porous, flexible support material having an adhesive surface on at least one side and which is sterile throughout, said adhesive surface being such that when contacted with a microorganism-containing surface, the microorganism will be adhered thereto.

The sheets of this invention can be used for the semi-quantitative identification of microorganisms.

DETAILED DISCUSSION

Surprisingly, it has been found that it is possible using the sheet of this invention to remove microorganisms virtually quantitatively from any surface to be tested, after a brief period of contact. The microorganisms adhere to the surface of the sheet and can then be placed together with the sheet on a sterile culture medium and incubated. Since the pick-off sheet of this invention is not a pick-off culture medium, it possesses unlimited stability even without special storage conditions. Moreover, the field of applicability of the sheet is not inherently restricted by the choice of a culture medium. This is not true of prior art culture medium pick-off sheets since only microorganisms which grow on the particular culture medium can be tested. On the contrary, the pick-off sheet of this invention is suitable for all applications.

The pick-off sheet of this invention consists either of a plastic with good adhesion or of a suitable support material which is provided on one or both sides with a layer of an adhesive such as a plastic. Suitable plastics with good adhesion include, for example, polyvinylpyrrolidone, polyethylene glycol, polyvinyl methyl ether and others which customarily are used, for example, for binding dust or as binders, thickeners, glues and adhesives.

The adhesivity of the surface to be contacted with the microorganism, of course, must be sufficient to remove the microorganisms from the test surface and adhere them to the sheet. Also, the adhesive surface must be of such a nature (e.g., porosity) that it permits the nutrient culture medium to contact with the adhered microorganisms during incubation. Typical adhesive layer thicknesses are 10–1000 $\mu$m. Typical substrate thicknesses, irrespective of whether the substrate has a separate adhesive layer, are 100–2500 $\mu$m.

Suitable support materials for the sheet of this invention having a layer of plastic having increased adhesion include, for example, paper, cellulose esters, polyvinyl chloride, glass fibers, gelatine, polyamide, polystyrene, plastic or textile fabrics, agar film and similar materials.

The support materials used as sheets should be porous; that is, water and relatively small molecules, such as the nutrients contained in the culture medium, should be able to diffuse into and through the sheet or to effect capillary penetration without hindrance. It is advantageous, but not absolutely essential, for the pores to be smaller than bacteria and to prevent these from penetrating into the substrate of the sheets. Suitable such substrates have average pore diameters of up to 0.5 $\mu$m.

Moreover, the sheet should be so flexible, bendable and foldable that it can adapt well to the shape of the article to be tested and can also, for example, be pressed into corners or narrow recesses.

The identification of and/or determination of the presence of the microorganisms using this pick-off sheet is effected, after contact with the test surface, by placing the sheet on a sterile conventional culture medium and incubating. The side containing the microorganisms is faced upwards, i.e., faces away from the culture medium. The nutrient-containing liquid penetrates through the porous structure of the sheet to the surface of the sheet and enables the microorganisms adhering thereto to develop into visible colonies. The colonies can be rendered more easily discernible by suitable conventional dyeing of the sheet or by the addition of conventional dyes to the culture medium. The composition of the culture medium is not critical and can be chosen via conventional considerations including the types of microorganisms suspected.

Preferably, one side of the pick-off sheets of this invention, i.e., the side opposite the adhesive surface to be contacted with the test surface, is provided with an applicator. This may be, for example, an easily removable layer of foam or a protective film, which may be handled to enable the pressing of the sheet onto the surface to be tested, and then stripped off and discarded. The pick-off sheet is then placed on a culture medium under customary aseptic conditions or is temporarily stored under sterile conditions. Suitable removable foams or films for use as such applicators include sheets made of polyurethane, polyether, or other foamed polymers.

These are typically removably bonded to the substrates by adhesives such as water soluble adhesives, preferably vegetable glues such as gum arabic, starch gum, cellulose ether etc.

The pick-off sheets of this invention are normally of overall dimentions of 1–20 cm × 2–20 cm × 0.1–2.5 mm; e.g., 2 cm × 6 cm × 0.5 mm; 6 cm × 6 cm × 0.5 mm or 2 cm × 3 cm × 0.3 mm.

They are packaged in containers so that both container and strip are sterile. Thereby, they have an essentially unlimited shelf life as long as the package integrity is maintained. Thus, they can be stored for months, years, etc.

By "sterile" herein is meant microorganism-free.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A filter fabric made of nylon with a mesh width of 1 $\mu$m is impregnated with a 50% solution of polyvinylpyrrolidone in water with the addition of 1% of polyethylene glycol. After drying, the pick-off sheet prepared in this way is packed and sterilized. For use, a sterile sheet is taken from the pack, placed briefly on the surface to be tested, pressure being applied, and stripped off again. Immediately, or after intermediate storage in a sterile pack, the pick-off sheet is placed on a culture medium for microorganisms, the side which has been in contact with the surface to be tested facing upwards. After incubating for 2 days at 30° C., colonies of bacteria can be discerned at the points at which a germ has been removed by the sheet from the surface tested. The colonies are evaluated by counting or are transinoculated for further investigation.

EXAMPLE 2

A cellulose ester sheet is coated on one side with a 20% solution of polyvinyl methyl ether in water, dried and cut into 60 × 20 mm strips. The strips are individually welded into polyvinyl chloride film and sterilized. For use, a strip is taken from the sterile pack and used in the manner described in Example 1 for picking off and for identifying microorganisms.

EXAMPLE 3

A sheet is prepared in the manner described in Example 1. On the side of the sheet opposite to the adhesive side which would be contacted with the test surface, a removable backing serving as an applicator is attached. The applicator consisting of a polyurethane foam of the same dimensions as the sheet and with a thickness of about 2 mm is bonded to the sheet by gum arabic.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of determining the presence of microorganisms on a surface which comprises
    contacting the surface to be tested for the presence of microorganisms with an adhesive side of a sheet consisting essentially of a porous, flexible support material having an adhesive surface on at least one side such that when contacted with a microorganism-containing surface, the microorganisms will be adhered thereto; removing the sheet from this surface; placing the sheet on a sterile culture medium for microorganisms, the side placed on the medium being that opposite the side which was in contact with the test surface; incubating the sheet; and analyzing the incubated sheet for the presence of microorganisms.

2. The method of claim 1, wherein the porosity of the support material is such that microorganisms cannot pass through the support material but a culture medium for microorganisms can pass through.

3. The method of claim 2, wherein the porosity of the support material is such that the average pore diameter is up to 0.5 $\mu$m.

4. The method of claim 3, wherein the sheet further comprises a sterile, removable backing on the side of the sheet opposite to the adhesive side, said removable backing serving as an applicator whereby the adhesive side may be contacted with the surface to be tested without otherwise contaminating the sheet.

5. A sheet for picking off microorganisms from a surface which comprises a porous, flexible support material having an adhesive surface on at least one side and which is sterile throughout, said adhesive surface being such that when contacted with a microorganism-containing surface, the microorganisms will be adhered thereto, wherein the porosity of the support material is such that microorganisms cannot pass through the support material but a culture meduim for microorganisms can pass through.

6. The sheet of claim 5, wherein the porosity of the support material is such that the average pore diameter is up to 0.5 $\mu$m.

7. The sheet of claim 5 which further comprises a sterile, removable backing on the side of the sheet opposite to the adhesive side, said removable backing serving as an applicator whereby the adhesive side may be contacted with the surface to be tested without otherwise contaminating the sheet.

8. A sterile container containing the sterile sheet of claim 7.

9. The sheet of claim 5 which further comprises a sterile, removable backing on the side of the sheet opposite to the adhesive side, said removable backing serving as an applicator whereby the adhesive side may be contacted with the surface to be tested without otherwise contaminating the sheet.

10. The sheet of claim 9, wherein the adhesive surface of the sheet is formed by adhering an adhesive layer to one side of the support material.

11. A sterile container containing the sterile sheet of claim 5.

12. The sheet of claim 5, wherein the adhesive surface of the sheet is formed by adhering an adhesive layer to one side of the support material.

* * * * *